(12) United States Patent
Boettinger et al.

(10) Patent No.: US 12,042,157 B2
(45) Date of Patent: Jul. 23, 2024

(54) FIXING CLAMP AND ALIGNING DEVICE (71) Applicant: Aesculap AG, Tuttlingen (DE)

(72) Inventors: Roland Boettinger, Rietheim-Weilheim (DE); Tim Meier, Essen (DE)

(73) Assignee: Aesculap AG, Tuttlingen (DE)

( * ) Notice: Subject to any disclaimer, the term of this patent is extended or adjusted under 35 U.S.C. 154(b) by 431 days.

(21) Appl. No.: 17/430,796

(22) PCT Filed: Feb. 13, 2020

(86) PCT No.: PCT/EP2020/053740
§ 371 (c)(1),
(2) Date: Aug. 13, 2021

(87) PCT Pub. No.: WO2020/165332
PCT Pub. Date: Aug. 20, 2020

(65) Prior Publication Data
US 2022/0160370 A1 May 26, 2022

(30) Foreign Application Priority Data
Feb. 15, 2019 (DE) ...................... 10 2019 103 880.4

(51) Int. Cl.
*A61B 17/15* (2006.01)
(52) U.S. Cl.
CPC ................. *A61B 17/157* (2013.01)
(58) Field of Classification Search
CPC ................................................. A61B 17/157
See application file for complete search history.

(56) References Cited

U.S. PATENT DOCUMENTS

| | | | |
|---|---|---|---|
| 4,621,628 A | 11/1986 | Brudermann | |
| 5,002,547 A | 3/1991 | Poggie et al. | |
| | (Continued) | | |

FOREIGN PATENT DOCUMENTS

| | | |
|---|---|---|
| CN | 205379351 U | 7/2016 |
| DE | 20105643 U1 | 6/2001 |
| | (Continued) | |

OTHER PUBLICATIONS

Office Action received in U.S. Appl. No. 17/296,830 dated Jan. 20, 2023, 31 pages.

(Continued)

*Primary Examiner* — Sameh R Boles
(74) *Attorney, Agent, or Firm* — Christopher A. Rothe; Culhane PLLC (57) ABSTRACT

An aligning device and a fixing clamp for an aligning device for fixing and clamping a body extremity. The fixing clamp includes a first clamp arm, a second clamp arm, and a support fork or trough. The support fork or trough includes first and second support legs. The clamp also includes a section for mounting on or connecting to an adjusting rod, and first and second articulation joints on the support fork. The first clamp arm is rotatably articulated at one of the articulation joints about a first rotational axis, and the second clamp arm is rotatably articulated at the other of the articulation joints about a second rotational axis. The first articulation joint is displaceably mounted on the first support leg, and/or the second articulation joint is displaceably mounted on the second support leg of the support fork or trough.

13 Claims, 5 Drawing Sheets

(56) References Cited

U.S. PATENT DOCUMENTS

| | | | |
|---|---|---|---|
| 5,049,151 A | 9/1991 | Durham et al. | |
| 5,197,944 A * | 3/1993 | Steele | A61B 17/157 606/86 R |
| 5,514,145 A | 5/1996 | Durham et al. | |
| 5,628,750 A | 5/1997 | Whitlock et al. | |
| 5,667,511 A | 9/1997 | Vendrely et al. | |
| 5,704,941 A | 1/1998 | Jacober et al. | |
| 6,162,228 A | 12/2000 | Durham | |
| 6,221,035 B1 | 4/2001 | Kana et al. | |
| 6,277,123 B1 * | 8/2001 | Maroney | A61F 2/4657 606/99 |
| 7,344,542 B2 | 3/2008 | Collazo et al. | |
| 7,785,330 B2 | 8/2010 | Sherman et al. | |
| 10,792,049 B2 | 10/2020 | Fiedler et al. | |
| 2005/0070910 A1 | 3/2005 | Keene | |
| 2005/0182415 A1* | 8/2005 | Steffensmeier | A61B 17/154 606/88 |
| 2006/0189998 A1 | 8/2006 | Rasmussen | |
| 2006/0241639 A1 | 10/2006 | Kuczynski et al. | |
| 2008/0027471 A1 | 1/2008 | Hauri | |
| 2010/0087831 A1 | 4/2010 | Marx | |
| 2012/0053594 A1 | 3/2012 | Pelletier et al. | |
| 2012/0101504 A1 | 4/2012 | Habegger et al. | |
| 2014/0324054 A1 | 10/2014 | Dmuschewsky et al. | |
| 2016/0367291 A1 | 12/2016 | Erickson et al. | |
| 2017/0245893 A1 | 8/2017 | Sanders et al. | |
| 2022/0008086 A1 | 1/2022 | Hirt et al. | |
| 2022/0022889 A1 | 1/2022 | Hirt et al. | |
| 2022/0160370 A1 | 5/2022 | Boettinger et al. | |

FOREIGN PATENT DOCUMENTS

| | | |
|---|---|---|
| DE | 69719663 | 11/2003 |
| DE | 69531388 | 6/2004 |
| DE | 69630776 T2 | 9/2004 |
| DE | 60028278 | 5/2007 |
| DE | 60212852 T2 | 8/2007 |
| DE | 102006035602 A1 | 2/2008 |
| DE | 202015101629 U1 | 7/2015 |
| DE | 102018130117 A1 | 5/2020 |
| DE | 102019103880 A1 | 8/2020 |
| EP | 0839501 A2 | 5/1998 |
| GB | 2398010 A | 8/2004 |
| JP | 2008125706 A | 6/2008 |
| JP | 2011092405 A | 5/2011 |
| WO | 0071035 A1 | 11/2000 |
| WO | 03013371 A1 | 2/2003 |
| WO | 2005110249 A1 | 11/2005 |
| WO | 2009037479 A1 | 3/2009 |
| WO | 2012027816 A1 | 3/2012 |
| WO | 2013134595 A1 | 9/2013 |
| WO | 2019046518 A2 | 3/2019 |
| WO | 2020013584 A1 | 1/2020 |
| WO | 2021209496 A3 | 10/2021 |

OTHER PUBLICATIONS

Search Report received in German Application No. 10 2019 103 880.4 dated Oct. 23, 2019, with translation, 16 pages.
Search Report received in International Application No. PCT/EP2020/053740 dated Oct. 9, 2020, with translation, 5 pages.
Written Opinion received in International Application No. PCT/EP2020/053740 dated Oct. 9, 2020, with translation, 9 pages.
International Search Report received in International Application No. PCT/EP2019/082960 dated Feb. 5, 2020, with translation, 5 pages.
International Search Report received in International Application No. PCT/EP2019/082964 dated Mar. 6, 2020, with translation, 10 pages.
Search Report received in German Application No. 10 2018 130 117.0 dated Sep. 5, 2019, with translation, 14 pages.
Search Report received in German Application No. 10 2018 130 119.7 dated Sep. 5, 2019, with translation, 11 pages.
Written Opinion received in International Application No. PCT/EP2019/082960 dated Feb. 5, 2020, with translation, 13 pages.
Written Opinion received in International Application No. PCT/EP2019/082964 dated Mar. 6, 2020, with translation, 9 pages.
Office Action received in Japanese Application No. 2021-546788 dated Feb. 25, 2022, with translation, 10 pages.
Non-final Office Action received in U.S. Appl. No. 17/296,676, dated Mar. 28, 2022.
Search Report received in German Application No. 10 2020 110 346.8 dated Dec. 11, 2020, with translation, 12 pages.
Search Report received in International Application No. PCT/EP2021/059647 dated Oct. 12, 2021, with translation, 10 pages.
Written Opinion received in International Application No. PCT/EP2021/059647 dated Oct. 12, 2021, with translation, 29 pages.

\* cited by examiner

FIXING CLAMP AND ALIGNING DEVICE

CROSS-REFERENCE TO RELATED APPLICATIONS

This application is the United States national phase entry of International Application No. PCT/EP2020/053740, filed Feb. 13, 2020, and claims the benefit of priority of German Application No. 10 2019 103 880.4, filed Feb. 15, 2019. The contents of International Application No. PCT/EP2020/053740 and German Application No. 10 2019 103 880.4 are incorporated by reference herein in their entireties.

FIELD

The present disclosure relates to a fixing clamp/fixing clip for an aligning device, in particular for a tibial resection, for fixingly clamping a body extremity of a patient, such as a tibia or a malleolus of a tibia, an ankle, a leg or a tarsal joint, comprising a first clamp arm and a second clamp arm and comprising a support fork or support trough for the body extremity having a first and a second support leg, which has a central mounting or connecting portion for mounting or connecting to an adjusting rod as well as a first rotation joint and a second rotation joint on the support fork, on each of which the corresponding first clamp arm is rotatably articulated or connected about a first rotational axis and the second clamp arm is rotatably articulated or connected about a second rotational axis. In addition, the invention relates to an aligning device/adjusting guide/extramedullary tibia-aligning (ETA) instrument for a tibial resection guide.

BACKGROUND

Precise resection of a patient's bone, in particular of the tibia, is of great importance for the success of surgery for implanting a joint prosthesis. The plane of the resection has to be precisely localized in order to minimize a degree of bone removal on the one hand, wherein on the other hand it has to be ensured at the same time that all of the defective bone tissue is removed. The alignment of the plane in relation to an anatomical axis, in particular a tibial axis, has to be continuously controlled during surgery in order to ensure the orientation of the articular surfaces of the joint over the entire range of joint motion.

The exact definition of a tibial resection plane in a knee joint is usually adjusted using an aligning device or adjusting guide (for a saw block) with a columnar adjusting rod, which is fixed remotely from the tibia near the ankle. The adjusting rod extends along the tibia (substantially) parallel to the corresponding anatomical tibial axis. The resection plane can then be defined in relation to the tibial axis. A saw block or guide block (cutting block/guiding device) attached to the aligning device finally defines the plane of the resection. Usually, the guide block has a through slot through which a reciprocating, planar cutting edge of a surgical instrument (saw) is passed.

In order to adjust the orientation of the tibial resection plane, a fixing clamp or fixing clip is attached near the patient's ankle, which is tied to the adjusting rod at its one end facing a patient's foot, at whose other end (end portion), the saw block/guide block is fixed/fixable.

U.S. Pat. No. 6,221,035 B1 discloses a (fixation) clamp for an alignment aid used in tibial resection. The clamp comprises two spring-preloaded clamp arms, which can be rotated about a respective rotational axis relative to a frame. These clamp arms are brought into an open position and, after contact with the tibia, are released via a manual actuation device. Due to the spring preload, they then enclose an ankle joint or the tibia and clamp it. The clamp arms are preloaded in the closing direction. The spring preload causes a force-fit fixation, but this has the disadvantage that hematomas may occur on the patient's body due to the clamping force. The clamp arms have a spring-loaded effect on the ankle joint or ankle. However, the fixing clamp is not adapted to a patient's anatomy, so that the clamp arms exert a different contact force depending on the shape of the foot and the thickness of the ankle joint. This also results in a holding force of the fixing clamp that depends on the shape of the ankle.

One problem of the prior art is that fixation to the patient's ankle is usually force-fitted or the clamp arms are preloaded in a force-fit manner, resulting in insufficient positionability due to the inherent elasticity of the clamp arms. There is no adaptation to the patient's anatomy. In the worst case, this leads to a detachable fixation, which, however, is not sufficient due to the high requirements for dimensional accuracy or precision in the orientation of the plane of the resection described at the beginning. Furthermore, the different clamping forces of elastically preloaded clamping arms can cause hematomas on the patient's body parts. Fixing clamps in the prior art do not cover all anatomical sizes, since the clamping force depends on the patient's particular anatomy. Therefore, different variants of fixing clamps would have to be manufactured and stored for optimal fitting, but this is not practiced in practice due to high costs and poor manageability. Fixing clamps that are spring-preloaded against the malleolus or ankle pose the problem that the spring applies a contact force that varies depending on the shape of the foot and the thickness of the ankle.

SUMMARY

It is therefore the object of the invention to avoid or at least reduce the disadvantages of the prior art and in particular to provide a fixing clamp as well as an aligning device which allow a simple, safe and quick fixation as well as simple and quick release of the fixation from a body extremity/limb, in particular at or around the ankle joint or around the tibia, wherein the fixing clamp and the aligning device are adapted for different anatomies of body extremities, in particular of the ankle joint, and can be used for any anatomy and avoid hematomas by their modes of operation and configurations. Furthermore, the fixing clamp should have a construction that is as simple as possible and which is preferably easy to assemble, clean and sterilize.

The core of the present invention therefore is in that the clamp arms articulated on the rotation joints are configured to be moved and positioned independently of each other on the corresponding support leg without tools on the support fork as the base body, which has two rigid support legs as struts arranged at an angle to each other. This means that the fixing clamp has rotational axes for the clamp arms that are adapted to be selectively positioned relative to the support fork.

In other words, a distance from the respective rotational axis of the clamp arms to a base point of the meeting support legs can be continuously adjusted between a minimum possible distance and a maximum possible distance and can thus be individually adapted to an anatomy. In particular, the rotation joint with the correspondingly articulated clamp arm can be displaced along a longitudinal axis of the corresponding support leg via a guide. In particular, the rotational axes (of the rotation joints) are perpendicular to a longitudinal axis of the support legs. Preferably, the two rotational axes of the two clamp arms are arranged parallel to each other. Alternatively, the rotational axes may also have a certain angle between them, in particular they may intersect.

If, for example, the clamp arms are spring-preloaded in a closing rotational direction, the holding force of the spring-preloaded clamp arms remains the same even if the rotation joints are displaced. This creates a constant holding force of the fixing clamp regardless of the anatomy of the foot, for example.

Specifically, the first rotation joint is displaceably/movably mounted on the first support leg and/or the second rotation joint is displaceably mounted on the second support leg of the support fork.

In terms of construction, the idea according to the invention is implemented in that the first and/or second support leg has a mechanical guide or a guide element in or with which the rotation joint is displaceably guided. The rotation joint is thus in form-fit operative engagement with the guide of the support leg, wherein only a translatory displacement at the support leg is permitted. Specifically, the support leg has a guide surface on which a corresponding sliding surface of the rotation joint can slide, wherein a corset structure slidably holds the rotation joint on the support leg. The corset structure can be configured in different ways. For example, the corset structure may be realized in that the rotation joint, viewed in the direction of the rotational axis, has two opposing, planar inner surfaces between which the support leg is enclosed. In this way, the rotation joint can be slid in a plane relative to the support leg. With the aid of the mechanical guide, for example in the form of a guide rail, a curve (trajectory curve) results from the plane due to the further geometric restriction. The corset structure may also be configured, for example, such that the support leg has two opposing inner surfaces between which the rotation joint is enclosed. The support leg of the fixing clamp thus has, on the one hand, sliding surfaces on which the rotation joints can slide and can be translationally displaced and, on the other hand, it has guide surfaces which, in particular, are perpendicular to the sliding surfaces in order to guide the rotation joint on the sliding surface along a predetermined path.

According to a preferred embodiment, the first rotation joint in the form of a d may be mounted on the first support leg displaceably but (substantially) rotationally fixed and/or the second rotation joint in the form of a pivot bearing is mounted on the second support leg displaceably but (substantially) rotationally fixed, so that an orientation of the corresponding pivot bearing with respect to the corresponding support leg is maintained even during a displacement. In other words, the rotation bearing itself, in which the clamp arm is mounted to be rotatable about the rotational axis, is secured against rotation via a support surface on both the rotation joint and the support leg. It can also be said that the rotation joint, as seen in cross-section, has to have at least one contour deviating from a circularly symmetrical shape as an abutment surface, in particular a contour with two parallel edges/sides, preferably a substantially rectangular contour, which in cooperation with a corresponding support surface of the support leg, one extension direction of which is parallel to the rotational axis, prevents rotation. Thus, an orientation of the rotation joint can be maintained.

Preferably, the displaceably mounted, first rotation joint and/or second rotation joint may have a self-retaining/self-locking mechanism relative to the support fork, which holds the first rotation joint or the second rotation joint frictionally and/or form-fittingly in at least one position relative to the support fork and inhibits a displacement movement. Such a self-retaining mechanism can be designed in different forms. For example, the rotation joint can be elastically preloaded to press the associated support leg between it and against it, so that frictional resistance acts as a self-retaining mechanism to hold the rotation joint in position. If the frictional resistance is removed, for example by manual operation, the self-retaining mechanism is canceled and the rotation joint can be displaced again. It is also conceivable, for example, that a screw which is screwed in particular into a thread of the rotation joint and whose end rests against the support leg applies an adjustable clamping force to the support leg and thus inhibits a displacement movement. Alternatively or additionally, the self-retaining mechanism can also have a form-fit design, for example by forming a latching mechanism between the rotation joint and the associated support leg.

According to a further preferred embodiment, the self-retaining mechanism can be activated and deactivated. This means that the self-retaining mechanism can be manually activated and deactivated and thus there are (at least) two different states of the self-retaining mechanism. In a case of, for example, a form-fit latching mechanism, this can be manually disengaged from operative engagement.

In particular, the self-retaining mechanism can be activated by a torque applied to the first rotation joint, in particular by transmission of the torque through the first clamp arm, or by a torque applied to the second rotation joint, in particular by transmission of the torque through the second clamp arm, by tilting/canting between the rotation joint and the support leg, and can be deactivated when the torque is removed. Similar to an adjustment option of a screw clamp, in which an angle is changed by rotation between two surfaces in such a way that they are no longer parallel but have an angle between them and thus become tilted, the rotation joint is also (slightly) rotated relative to the associated support leg in the self-retaining mechanism. The rotation joint preferably has two (at least partially) parallel control surfaces, which are guided in the support leg enclosed by parallel inner surfaces, wherein the control surfaces do not lie directly against the support leg, but have a slight clearance. If the rotation joint is now rotated as a result of an applied torque, the control surfaces or edges of the control surfaces lie directly against the inner surfaces of the support legs and a frictionally-engaged connection is established.

Preferably, the first rotation joint and/or the second rotation joint can be displaceably guided via a guide block in an elongated hole formed in the corresponding first support leg or second support leg. The elongated hole, which has two parallel, opposite inner surfaces, encloses the guide block of the rotation joint, wherein the guide block also has two parallel control surfaces. A small gap is formed between the control surfaces and the inner surfaces, or there is a clearance, so that it is also possible to rotate the control surfaces relative to the inner surfaces of the elongated hole. Thus, the guide block can be slidingly guided in the elongated hole as long as the control surfaces and the inner surfaces are parallel to each other, and when the guide block, which is rotationally and axially fixed to the rotation joint, is rotated, they become tilted and the self-retaining mechanism is activated and inhibits a sliding movement of the rotation joint in the support leg.

It may be expedient if the first clamp arm and/or the second clamp arm is/are preloaded via a torsion spring, in particular via a coil spring, in a closing rotational direction or in an open(ing) rotational direction. A defined contact pressure can be transmitted to the clamp arm via the coil spring. For this purpose, the coil spring is fastened on the one hand to the rotation joint, which is guided in a rotationally-fixed manner on the support leg, and on the other hand it presses against the clamp arm and preloads it elastically, in particular in the closing rotational direction. This allows a foot to be spring-preloaded in the fixing clamp with a defined spring force.

According to a further aspect of the invention, the first clamp arm and/or the second clamp arm may be frictionally and/or form-fittingly held or locked in at least one position relative to the support fork via a rotary self-retaining mechanism, preferably in the form of a latching mechanism, and can block a movement of the first and/or of the second clamp arm about the respective rotation joint in an open rotational direction and/or a closed rotational direction. In particular, the latching mechanism, which latches the first clamp arm and/or the second clamp arm relative to a base, referred to as a support fork, can be locked form-fittingly in at least one position, preferably in a plurality of selectable pivot positions, and can block a pivot movement of the first or second clamp arm about the respective rotation joint in an open rotational direction. The open rotational direction is the direction of rotation in which the (tips of the) clamp arms move away from each other in order to open the fixing clamp. Due to the form-fit locking and blocking of the open rotational direction of the clamp arms, a user can discretely adjust the clamping or the geometric fixation of the clamp arms and thus ultimately the clamping force. A clamping spring is no longer required for force-fit fixation, but fixation is achieved/held in a form-fit manner by the latching mechanism. The user can therefore manually press the clamp arms together (in the closing rotational direction) and lock them in at least one position via the latching mechanism. When the clamp arms are in contact around an ankle joint, their geometry allows them to press lightly against it, for example in conjunction with the elasticity of the body tissue, in order to achieve a tight fit. Hematoma formation can be prevented, however, since no spring preload is applied which would press the clamp arms further together in the closing rotational direction beyond an uncontrolled, possibly excessive clamping force. Furthermore, the user does not have to press the clamp arms apart again against the preload force, but he/she can move the clamp arms back to their original position when the form fit is released in a certain way. This improves handling. It also does not have to be ensured that the spring force always corresponds to a predetermined value and, in particular, does not lose its preload over a period of time. This also simplifies or eliminates the need for maintenance.

In a preferred embodiment, the rotary self-retaining mechanism can be configured in the form of a ratchet mechanism or a freewheel in order to lock the open rotational direction of the associated clamp arm via form fit, wherein a detent of the ratchet mechanism is deflected against its preload via an actuating body, and the form fit and thus the operative engagement of the detent is released, so that the associated clamp arm is freely rotatable about its rotational axis. A ratchet mechanism with a ratchet wheel (gear wheel) and a (spring-preloaded) detent is a particularly suitable configuration in which a special geometric shape of the teeth permits rotary movement in one direction and locks in the opposite direction of rotation. The ratchet mechanism allows the corresponding clamp arm of the fixing clamp to move in the closing rotational direction and locks the opposite movement in the open rotational direction. Such a system is similar in function to a pawl mechanism in which a detent engages a ratchet wheel in a spring-preloaded manner. The actuating body additionally allows the user to manually release or unlock it. For this purpose, the actuating body can be moved translationally, in particular along the corresponding support leg, wherein an abutment surface deflects the detent against its preload in a position-dependent manner, the ratchet mechanism disengages (form-fittingly) from its operative engagement and is thus deactivated. If the actuating body is released again, the detent returns to its 'normal state' of operative engagement, in particular due to a preload, and the latching mechanism in the form of the ratchet mechanism is then activated again.

The object of the invention is solved according to the invention in that a fixing clamp according to the invention is used in a generic aligning device for a tibial resection guide for use in preparing a knee joint for implantation of a prosthesis, comprising an adjusting rod which is alignable with respect to a tibia of a patient, a guiding device at one end of the adjusting rod adapted to guide a tool during a resection of the tibia, and a fixing clamp arranged at an opposite end of the adjusting rod or towards the other end of the adjusting rod, which grips and fixes the patient's tibia in order to fix the adjusting rod in relation to the tibia. The aligning device can be quickly and easily oriented and positioned on a shinbone or with respect to a tibia of the patient using the fixing clamp according to the invention and can be released again just as easily in order to reposition or remove the aligning device. Handling is significantly simplified and hematomas are prevented.

BRIEF DESCRIPTION OF THE DRAWING FIGURES

The present invention is explained in more detail below on the basis of preferred embodiments with reference to the accompanying figures.

The figures are merely schematic in nature and are intended only to aid understanding of the invention. Identical elements are provided with the same reference signs. The features of the various embodiments can be interchanged.

DETAILED DESCRIPTION

FIGS. 1 to 6 show in a perspective view, in a top view, in a side view, in a longitudinal sectional view, in a sectional view and in a perspective rear view a first preferred embodiment of a fixing clamp 1 according to the invention for an aligning device (not shown). The fixing clamp 1 has a rigid Y-shaped support fork 2 formed (rotationally) symmetrically to a symmetric axis S with a first support leg 4 and a second support leg 6, which is formed in the manner of a support trough in order to receive and support a body extremity of a patient geometrically between itself or resp. the two support legs 4, 6, respectively. A first rigid clamp arm (clamping finger) 12 is indirectly attached or articulated to the first support leg 4 via a first rotation joint 8 and a second rigid clamp arm (clamping finger) 14 is indirectly attached or articulated to the second support leg 6 via a second rotation joint 10, in each case rotatable about a corresponding first rotational axis D1 or a second rotational axis D2, wherein according to the invention the first rotation joint 8 together with the first clamp arm 12 and the second rotation joint 10 together with the second clamp arm 14 can be displaced and positioned on the respective support leg 4, 6 along its respective longitudinal axis.

For this purpose, end portions 16 of the two support legs 4, 6 are each fork-shaped/groove-shaped when viewed from the side (see FIG. 3), or have a gap/recess 20 between two planar, parallel (inner) surfaces/guide surfaces 18 of the support leg 4, 6 facing the clamp arms 12, 14 when viewed in the direction of the rotational axes D1, D2. In this recess 20 of the fork-shaped end portions 16, the associated clamp arm 12, 14 is framed with planar (outer) surfaces/guide surfaces 21 in the manner of a hinge. The guide surfaces 18, 21 lie flat on each other and allow movement in one plane. A hinge pin 22 protrudes through an upper elongated hole 24 (seen in FIG. 3) of the end portion 16, through the associated clamp arm 12, 14, as well as through a further lower elongated hole 24 (seen in FIG. 3) that is congruent with the upper elongated hole 24 or aligned therewith. The hinge pin 22 thus forms the respective rotation joint 8, 10 together with the hinge-like enclosure of the clamp arm 12, 14 in the fork-shaped end portions 16 of the support leg 4, 6, wherein the rotation joints 8, 10 can be translationally displaced with respect to the support fork 2 due to the guidance of the respective hinge pin 22 in the two associated elongated holes 24.

In other words, the end portions 16 of the support fork 2 are formed as a fork joint, but with the difference that the fork joint does not have the two circular, aligned through holes, but that the fork joint instead has the two aligned elongated holes 24, the width of which corresponds to the diameter of the hinge pin 22, so that the hinge pin 22 can be guided in a translational manner in the elongated holes 24 in a longitudinal direction of the support legs 4, 6.

In the following, the function inherent in the fixing clamp 1 is explained according to the first preferred embodiment. Specifically, the fixing clamp 1 is prepared as an assembly to be used in the aligning device and to serve there as a geometric fixation of a fixing point of the aligning device. In order to achieve a large distance and a long lever arm for a highly accurate adjustment, the fixing clamp is placed close to the ankle and is connected to an end portion of an adjusting rod facing the patient's foot of the aligning device. More specifically, the support fork 2 is indirectly detachably attached to the adjusting rod of the aligning device (not shown) via a rigid mounting or connecting portion 26, and the ankle is inserted or placed into the rigid support fork 2.

According to the invention, both the first rotation joint 8 can be moved translationally along the first support leg 4 and (independently thereof) the second rotation joint 10 along the second support leg 6, so that a position of the rotation joints 8, 10 on the support fork 2 can be adjusted by a user such as a doctor. Thus, a distance from the first rotation joint 8 and from the first rotational axis D1 relative to a base point 28 of the Y-shaped support fork 2, where the two support legs 4, 6 meet, can be continuously adjusted within geometrically predetermined limits. Analogously, independent of the positioning of the first rotation joint 8, the second rotation joint 10 can be moved and adjusted along the second support leg 6.

In other words, the first rotation joint 8 is displaceably mounted on the first support leg 4 and the second rotation joint 10 is displaceably mounted on the second support leg 6 of the support fork 2. Via these two independently adjustable parameters of the distance of the rotational axis D1, D2 to the base point 28 of the support fork 2, the fixing clamp 1 can be individually adapted to a patient's anatomy. In this way, it can be ensured that the geometrically predetermined clamp arms 12, 14, which have a concave abutment surface 30, are adapted as optimally as possible to a geometric shape of a malleolus of a tibia. In particular, substantially different gripping diameters of the fixing clamp 1 can be adjusted. When the clamp arms 12, 14 are closed, the support fork 2 and the clamp arms 12, 14 form a frame that fits as closely as possible to the anatomical circumference of the ankle. The user is thus provided with further geometric adjustment options by the displacement options of the rotational axes D1, D2 on the corresponding support legs 4, 6, which do not yet exist in the prior art.

The configuration of the rotation joints 8, 10 is explained in detail below with the aid of FIG. 4, which shows a longitudinal section B-B through the hinge pin 22. The hinge pin 22 has essentially five different and directly consecutive or adjacent portions along its longitudinal axis. The construction and function are explained with reference to the second clamp arm 14 and the second support leg 6, wherein the first clamp arm 12 and the first support leg 4 have a corresponding analogous construction due to point symmetry with respect to the symmetric axis S.

Figure 4:
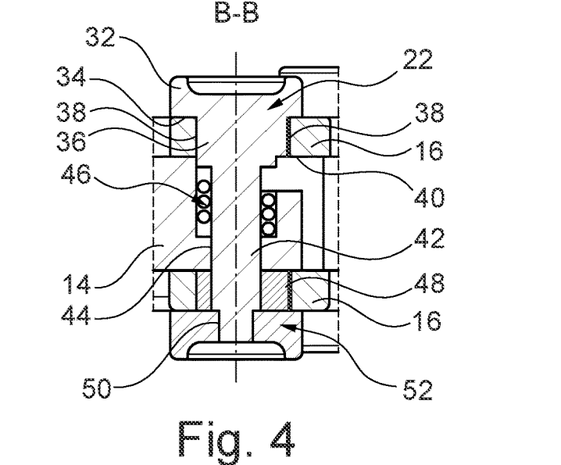
FIG. 4 shows a longitudinal sectional view through a rotation joint of the fixing clamp from FIGS. 1 to 3.

Specifically, it has as a first portion (top portion as seen in FIG. 4) a circular and rotationally symmetrical hinge head 32 whose diameter is larger than the width of the elongated hole 24 in order to be slidably guided on planar support surfaces 34 of the hinge head 32 on the end portions 16 and to axially limit the hinge pin 22 in the longitudinal direction as an undercut.

Directly following, a guide block 36 is formed as a second portion on the hinge head 32. This guide block 36 has two parallel, planar control surfaces 38, which are opposite the longitudinal axis of the hinge pin 22. The distance between the two control surfaces 38 is smaller than the diameter of the hinge head 32 and slightly smaller than the width of the elongated hole 24. Specifically, the two parallel, planar control surfaces 38 are bordered by two opposite, long inner surfaces of the elongated hole 24, wherein, however, a small gap 40 or a small distance is provided between the control surfaces 38 and the two opposite inner surfaces of one elongated hole 24. Thus, the guide block 36 has a clearance in the direction transverse to the longitudinal axis of the support legs 4, 6. If the hinge pin 22 is rotated in the elongated hole 24, the control surfaces 38 of the hinge pin 22 and the inner surfaces of the elongated hole 24 are no longer parallel to each other due to the clearance, but they have a (small) angle between them. This causes the outer edges of the control surfaces 38, which are diametrically opposed to the longitudinal axis, to contact and tilt against the two opposite inner surfaces of the elongated hole 24. Due to the frictional engagement, the respective rotation joint 8, 10 can no longer be displaced, whereby the self-retaining mechanism is realized. Thus, if the hinge pin 22 is (minimally) rotated in the elongated hole, for example by applying a torque to the hinge pin 22, this inhibits a displacement movement of the hinge pin 22 and thus of the associated rotation joints 8, 10 in the support fork 2 in a frictionally engaged manner. In addition, of course, the inner surfaces of the elongated holes 24 and/or the control surfaces 38 of the hinge pin 22 can be configured in such a way that, in addition to a frictionally engaged connection, there is also a form-fit connection that further supports tilting. For example, the respective surface can have a corrugated structure.

As a third portion, a cylindrical corrugated portion 42 follows the guide block 36 in the longitudinal axis direction of the hinge pin 22, around which the respective clamp arm 12, 14 is rotatably supported about the corresponding rotational axis D1, D2. As can be seen in FIG. 4, however, not the entire corrugated portion 42 serves for supporting the corresponding clamp arm 12, 14, but only a lower partial area of the circular corrugated portion 42 is embraced by a corresponding circular opening 44 of the clamp arm 12, 14. The remaining area of the corrugated portion 42 is surrounded by a coil spring 46. One end portion of the coil spring 46 is fixed to the guide block 36 on the one hand and another end portion of the coil spring 46 is arranged on the clamp arm 12, 14 in such a way that the coil spring 46 preloads the clamp arm 12, 14 in a closing rotational direction (a rotational direction in which the clamp arm 12, 14 is moved towards the other clamp arm 12, 14; a rotational movement towards the symmetric axis S).

If a force is applied to the respective clamp arm 12, 14, for example by deflecting it in an open rotational direction, the coil spring 46 transmits this force to the guide block 36. Since the force acts in a plane perpendicular to and offset from the longitudinal axis of the hinge pin 22, a torque is transmitted to the guide block 36 and it rotates relative to its elongated hole 24 as an enclosure. The guide block 36 tilts in the elongated hole and inhibits or prevents the displacement option of the rotation joint 8, 10 along its associated support leg 4, 6.

Thus, the following function is possible: the user can move the rotation joints 8, 10 with the clamp arms 12, 14 freely and without tools along the support legs 4, 6 until he/she reaches a desired position, then he/she can apply a force, in particular in the open rotational direction, to the clamp arms 12, 14, i.e. press against them, and thus inhibits or prevents a further change in position of the rotation joint 8, 10 with the force. This means that the rotation joints 8, 10 can be displaced until a load is applied to the clamp arms 12, 14 about the rotational axes D1, D2. The greater the force, the more the guide blocks 36 tilt in the elongated holes 24 and prevent a displacement movement. Regardless of the position of the rotation joints 8, 10 of the clamp arms 12, 14, however, a spring force remains the same. In this way, a firm hold of the fixing clamp 1 can be achieved in the region of the patient's ankle irrespective of a foot shape.

The user can apply the fixing clamp 1 to the malleoli or above or below or in the area of the malleoli, the clamp arms 12, 14 are pushed apart by the foot shape in the open rotational direction against the preload of the coil spring 46, the hinge pin 22 tilts due to the torque transmitted by the coil spring 46 and the rotation joints 8, 10 remain in their position relative to the support legs 4, 6.

The corrugated portion 42 is followed by a further guide block 48, which again, like the guide block 36, has the planar, parallel control surfaces 38, which are guided in the elongated hole 24, and the gap 40 between the control surfaces 38 and the inner surfaces of the elongated hole 24. The additional guide block 48 is plugged onto the hinge pin 22 for good assembly and is connected to it in a rotationally fixed manner. This additional guide block supports the tilting and serves as a bearing of the hinge pin 22 in the elongated hole 24.

As the fifth and last portion (lowest portion as seen in FIG. 4), the hinge pin 22 has an outer thread 50, which engages in an inner thread of a nut 52, which has the same diameter as the hinge head 32. This allows the rotation joint 8, 10 to be easily assembled, since the diameters or distances decrease gradually from the first portion to the fifth portion. Thus, the hinge pin 22 can be axially fixed through the upper elongated hole 24 seen in FIG. 4, through the coil spring 46, through the associated clamp arm 12, 14, through the lower elongated hole 24 seen in FIG. 4 and then with the nut 52. The hinge head 32 and the nut 52 have a trough or indentation in the longitudinal direction so that they can be easily gripped and moved with the thumb and forefinger.

Figure 1:
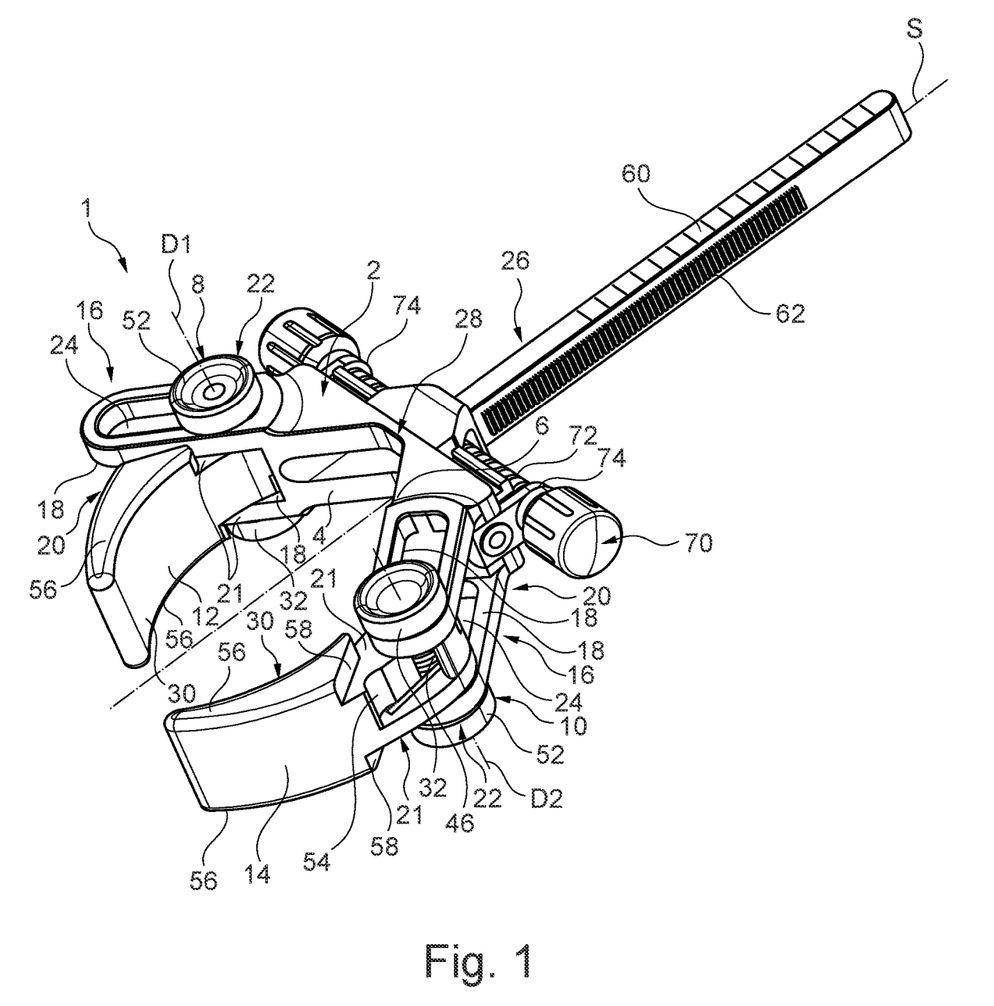
FIG. 1 shows a perspective view of a fixing clamp according to the invention in accordance with a first preferred embodiment.

As shown in FIG. 1, for example, the clamp arms 12, 14 are finger-shaped, wherein an indentation 54 is formed opposite the concave abutment surface 30 and in the area of the rotational axis. One end portion of the coil spring 46 rests in this indentation 54. In addition, an arm expansion 56 with stop 58 is formed in the region of the tips of the clamp arms 12, 14, at the level of the two elongated holes 24 formed in the support leg 4, 6. As can be seen, for example, in FIGS. 1 and 2, the stop 58 limits an angle of rotation about the rotational axis D1, D2 when the rotation joint 8, 10 is arranged near the base point 28.

The guide blocks 36, 48 are configured with a semicircular contour towards the tips of the support leg 4, 6, so that when the rotation joint 8, 10 is displaced in a position with maximum possible distance to the base point 28, they lie in the corresponding semicircular contour of the elongated hole 24.

Figure 2:
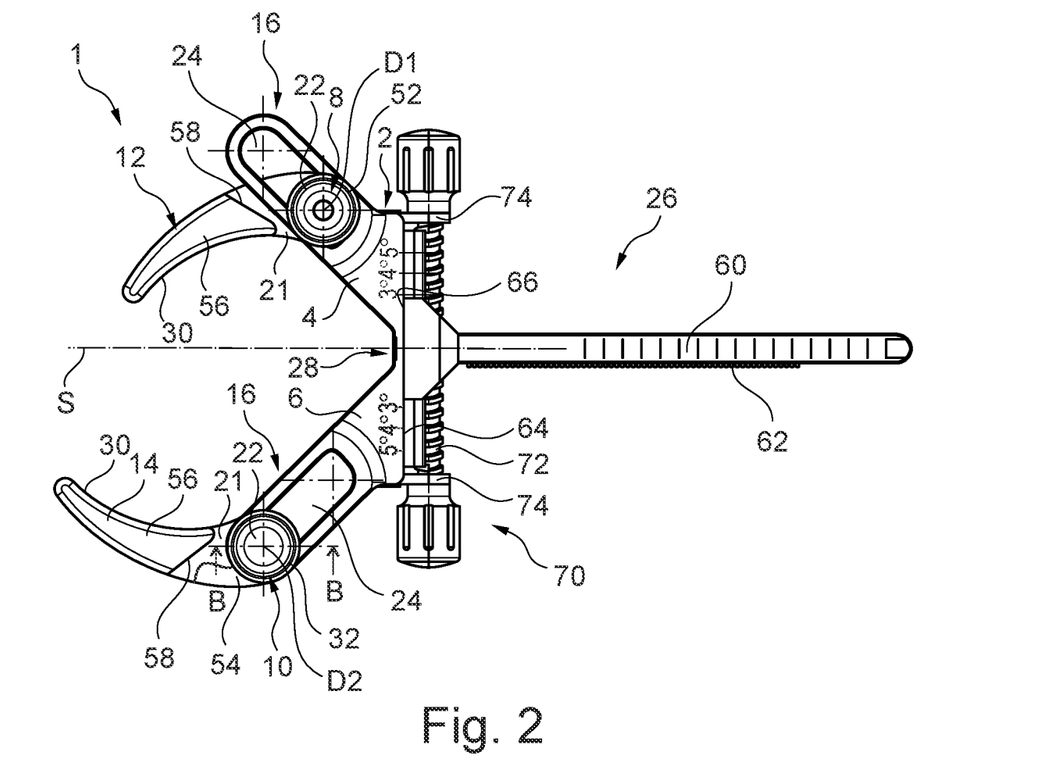
FIG. 2 shows a top view of the fixing clamp of FIG. 1.
Figure 3:
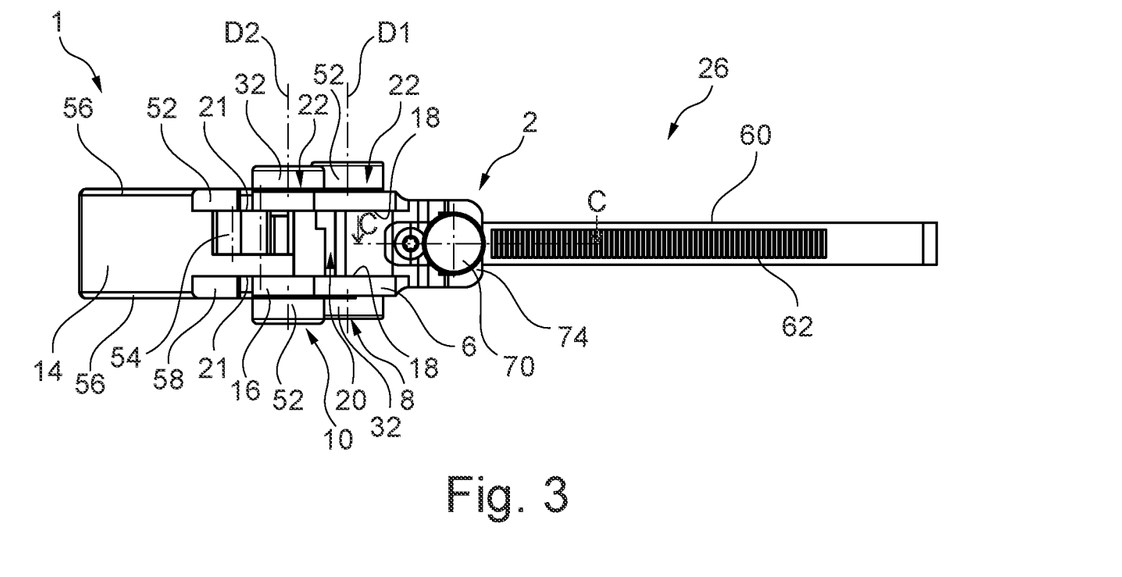
FIG. 3 shows a side view of the fixing clamp from FIGS. 1 and 2.

In FIGS. 1 and 2, the fixing clamp 1 is shown in a (partially opened) state. The clamp arms 12, 14 can be rotated and opened in the open rotational direction about their rotational axis D1, D2, and in this state the fixing clamp can be arranged on the malleoli (or above or below them) of the patient's tibia to later embrace/enclose them.

The fixing clamp 1 has a block-shaped, elongated cantilevered arm/cantilever beam 60 as a mounting or connecting portion 26 for connection/fixing/assembly to the adjusting rod. A latch structure 62 in the form of a gear rack is formed on a side surface of the cantilevered arm 60. The cantilevered arm 60 can be longitudinally displaced relative to the adjusting rod in order to adjust a position in the sagittal plane or an offset between the fixing clamp 1 and the aligning device, and can be form-fittingly fixed via the latch structure 62.

In the preferred embodiment, the Y-shaped support fork 2 is made in two parts, wherein the two support legs 4, 6 form one part as the fork head and the mounting or connecting portion 26 forms the other part.

The fork head has a flat sliding surface 64 on the side facing the connection section 26, which can slide translationally in an adjustment direction on a planar sliding surface 66 of the connection section 26. In order to be connected to the connection section 26 so that it can only move axially in the adjustment direction, the fork head has two L-shaped guide strips or guide projections 68, which are each enclosed and embraced by guiding hooks/grips 69 of the connection section 26, similar to a guide rail.

Figure 5:
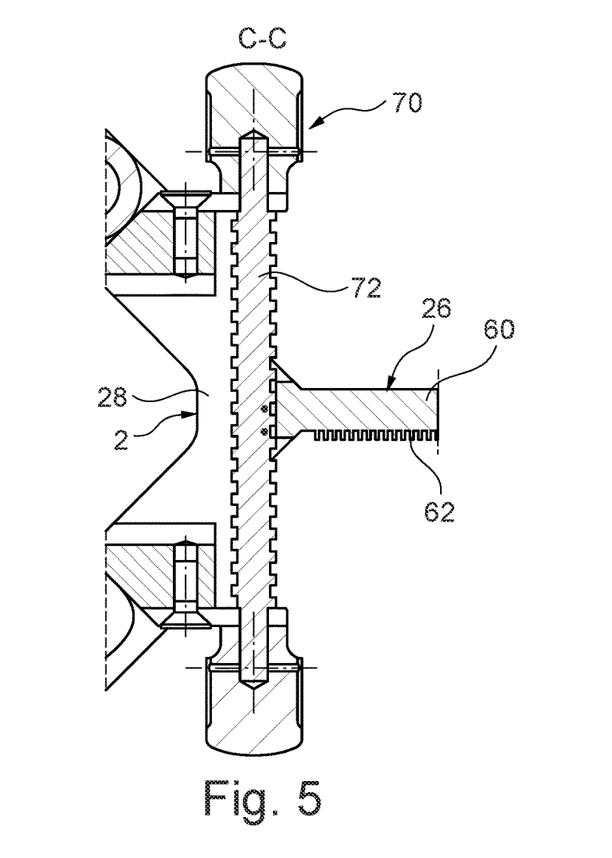
FIG. 5 shows a sectional view through a support fork of the fixing clamp of FIGS. 1 to 4.
Figure 6:
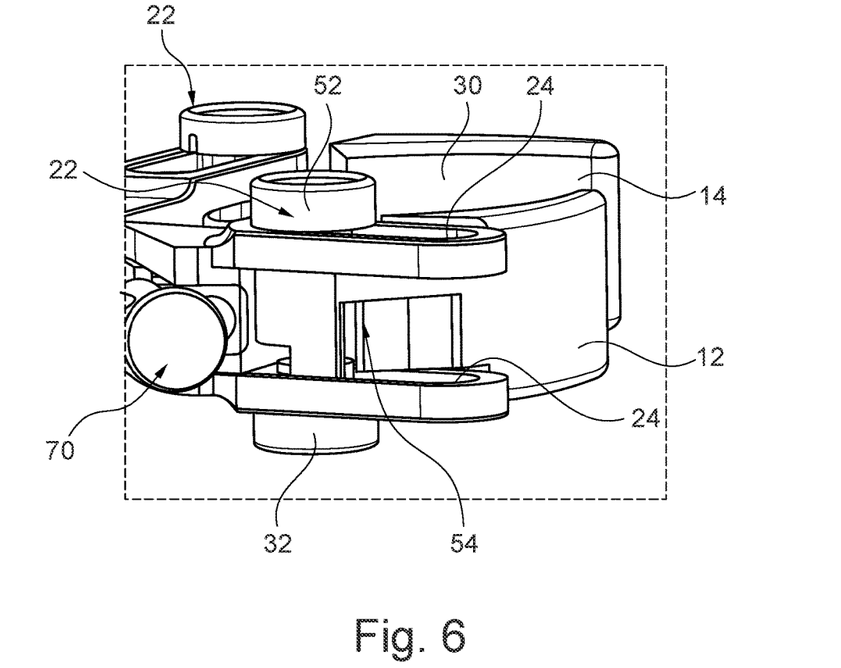
FIG. 6 shows a partial perspective view of the clamp arms of the fixing clamp from FIGS. 1 to 5.

As shown in FIG. 5, the fork head further includes a fulcrum shaft 70 as a rotational adjustment. A rotatable threaded pin 72 or threaded spindle 72 with outer thread engages in an (adapter) block with inner thread, which is attached to the connection portion. The threaded pin 72 further protrudes through a borehole of a crosspiece 74 and is axially fixed to the fork head by the latter, so that a rotation of the threaded pin 72, corresponding to the pitch of the outer thread, causes a translational displacement of the block and thus of the fork head in the adjustment direction. This allows the orientation of the fork head to the connection section 26, and thus also to the cantilevered arm 60, to be adjusted. Thus, the fixing clamp 1 of the aligning device can cause, among other things, an adaptation of the inclination of a guiding device and thus of the resection plane.

Figure 7:
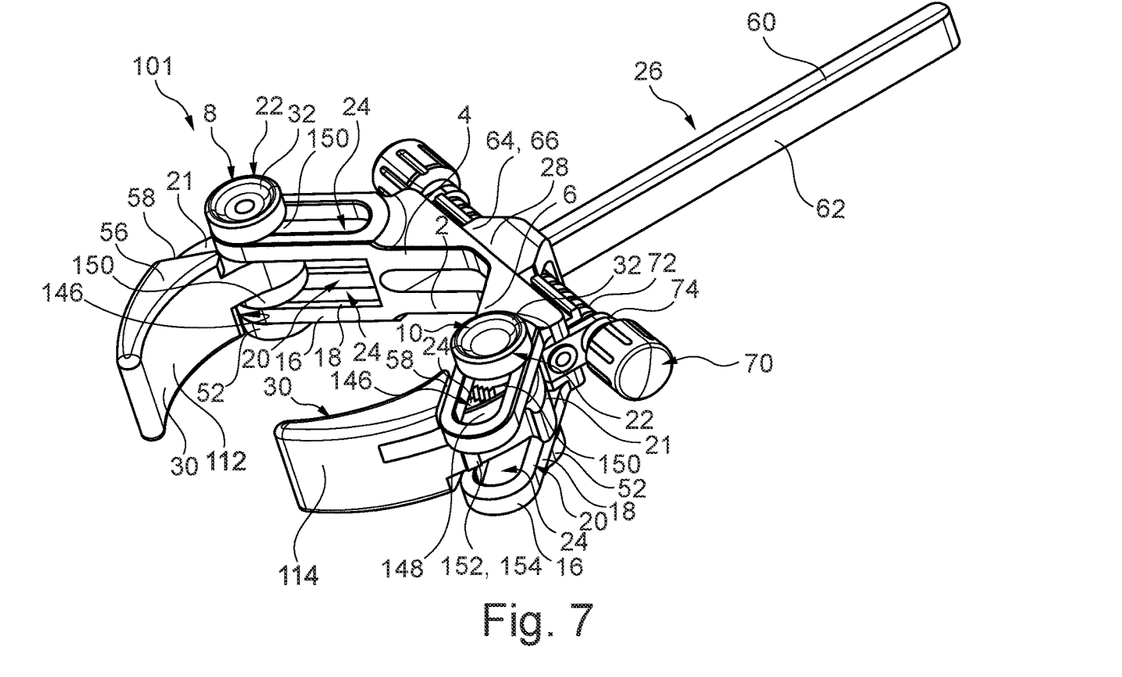
FIG. 7 shows a perspective view of a fixing clamp according to the invention according to a further, second preferred embodiment.
Figure 8:
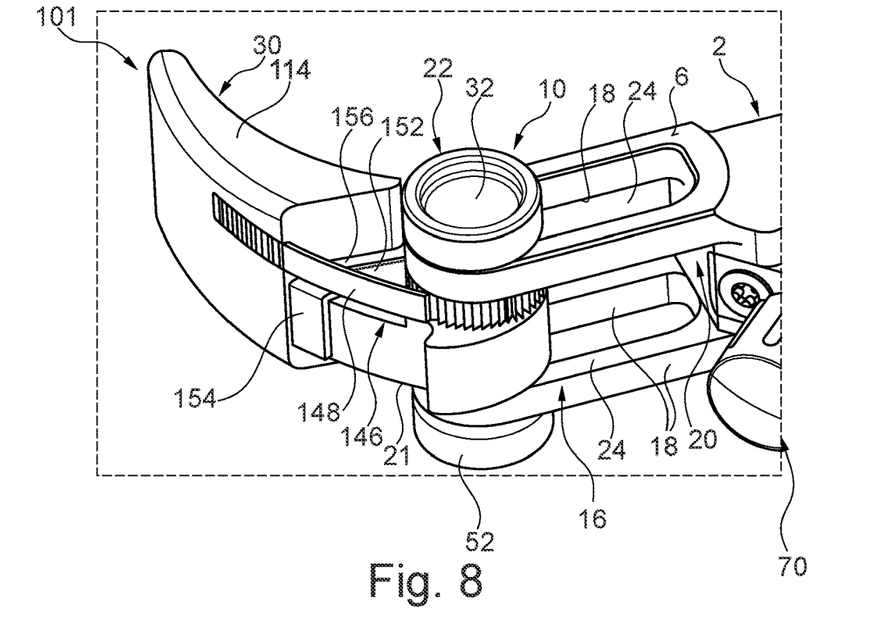
FIGS. 8 and 9 show detailed perspective views of the bearing of the clamp arms of the fixing clamp according to the second embodiment in FIG. 7.
Figure 9:
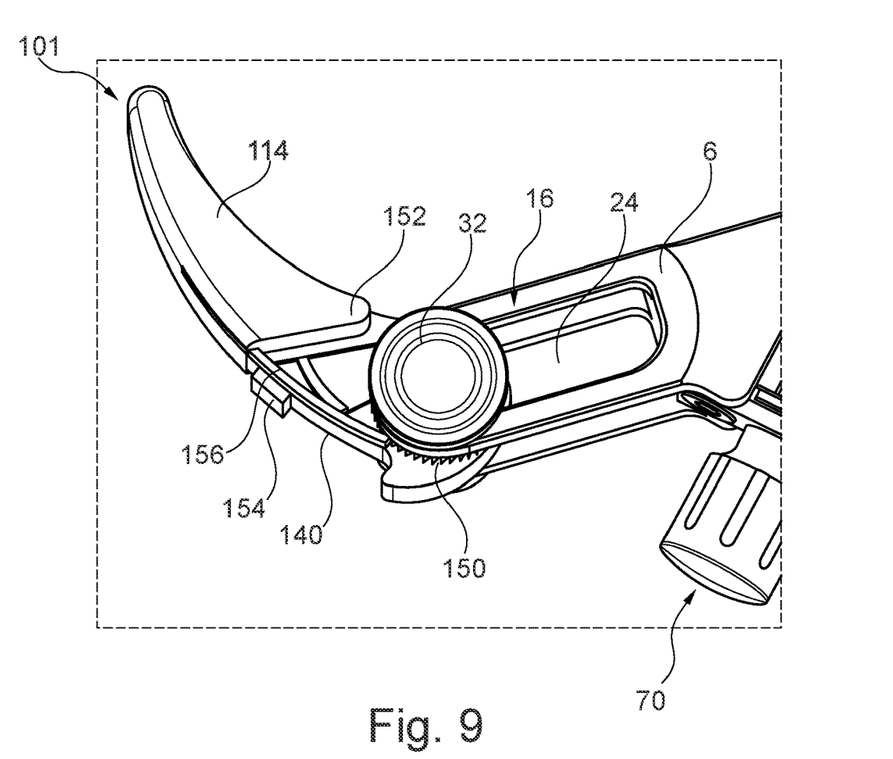

FIGS. 7 to 9 show a fixing clamp 101 according to a further, second preferred embodiment. The fixing clamp 101 corresponds essentially to the fixing clamp 1 of the first preferred embodiment, with the difference that instead of the clamp arms 12, 14, which are clamped force-fittingly via the coil spring 46, clamp arms 112, 114 are now used, which now enable a form-fitting latching mechanism. More precisely, the fixing clamp 1 has a ratchet mechanism 146 for holding the clamp arms 112, 114, wherein it is pointed out at this point that the latching mechanism or holding mechanism can also be a frictionally engaged mechanism.

The ratchet mechanism 146, as a form of a rotary self-retaining mechanism, locks the associated clamp arm 112, 114 in the open rotational direction, wherein a respective detent 148 attached to the clamp arm 112, 114 engages in a latch structure in the form of a gear wheel 150, which is connected in a rotationally fixed manner to the hinge pin 22 and is thus also indirectly connected in a rotationally fixed manner to the support fork 2. The detent 148 is in the form of a plate whose end portion (edge) presses into the teeth of the gear wheel 150 in a preloaded manner. The gear wheel 150 in turn has sawtooth-shaped projections with asymmetrical tooth flanks. Thus, a ratchet is formed by the detent 148 and the gear wheel 150, which on the one hand allows the detent 148 to slide on the gear wheel 150 in the closing rotational direction and on the other hand prevents the clamp arms 112, 114 from being moved in the open rotational direction.

Via an actuation lever 152 in the form of an eccentric lever, the detent 148 can be deflected against its preload and can be disengaged from the operative engagement so that the associated clamp arm can rotate freely about its rotational axis. Specifically, the actuation lever 152 is mounted on the respective associated clamp arm 112, 114 so as to be rotatable about a rotational axis. An actuation portion 154 is located on an outer surface of the clamp arm 112, 114 and can be manually pulled toward the associated rotation joint 8, 10. The actuation lever 152 rotates about the rotational axis, wherein an eccentric portion 156 formed on the actuation lever disengages and releases the detent 148 from an operative engagement. The clamp arm 112, 114 is free to rotate in the open rotational direction.

The invention claimed is:

1. A fixing clamp for an aligning device for fixingly clamping a body extremity, the fixing clamp comprising:
    a first clamp arm;
    a second clamp arm; and
    a support fork or support trough for the body extremity having:
        a first support leg, a second support leg, and a central mounting or connecting portion for mounting or connection to an adjusting rod, and
        a first rotation joint on the first support leg and a second rotation joint on the second support leg on the support fork, wherein the first clamp arm is rotatably articulated about a first rotational axis on the first support leg, and the second clamp arm is rotatably articulated about a second rotational axis on the second support leg, and
    wherein the first rotation joint is displaceably mounted on the first support leg in order to adjust the first rotational axis of the first rotation joint relative to the first support leg and/or the second rotation joint is displaceably mounted on the second support leg of the support fork in order to adjust the second rotational axis of the second rotation joint relative to the second support leg.

2. The fixing clamp according to claim 1, wherein the first rotation joint comprises a first pivot bearing and is mounted on the first support leg displaceably but rotationally fixed and/or the second rotation joint comprises a second pivot bearing and is mounted on the second support leg displaceably but rotationally fixed, so that an orientation of the first pivot bearing with respect to the first support leg and/or an orientation of the second pivot bearing with respect to the second support leg is maintained even during a displacement.

3. The fixing clamp according to claim 1, wherein the first rotation joint and/or second rotation joint has a self-retaining mechanism relative to the support fork or support trough, which respectively holds the first rotation joint and/or the second rotation joint frictionally and/or form-fittingly in at least one position relative to the support fork and inhibits a displacement movement.

4. The fixing clamp according to claim 3, wherein the self-retaining mechanism is adapted to be activated and deactivated.

5. The fixing clamp according to claim 3, wherein the self-retaining mechanism is activated by a torque applied to the first rotation joint respectively by a torque applied to the second rotation joint about the rotational axis by tilting between the rotation joint and the associated support leg and is deactivated when the torque is removed.

6. The fixing clamp according to claim 1, wherein the first rotation joint and/or the second rotation joint is displaceably guided via a guide block in an elongated hole formed in the first support leg and/or second support leg, respectively.

7. The fixing clamp according to claim 1, wherein the first clamp arm and/or the second clamp arm is preloaded via a torsion spring in a closing rotational direction or in an opening rotational direction.

8. The fixing clamp according to claim 1, wherein the first clamp arm and/or the second clamp arm frictionally and/or form-fittingly holds or locks in at least one position relative to the support fork or support trough via a rotary self-retaining mechanism and blocks a movement of the first clamp arm and/or the second clamp arm about the first rotation joint and/or second rotation joint, respectively, in an opening rotational direction and/or a closing rotational direction.

9. The fixing clamp according to claim 8, wherein the rotary self-retaining mechanism comprises a ratchet mechanism or a freewheel to lock the opening rotational direction via form fit, wherein a detent of the ratchet mechanism comprises a preload and is deflected against the preload via an actuation lever, and the form fit and the operative engagement of the detent are released, so that the first clamp arm and/or second claim arm is freely rotatable about its rotational axis.

10. The fixing clamp according to claim 8, wherein the rotary self-retaining mechanism comprises a latching mechanism.

11. The fixing clamp according to claim 1, wherein end portions of the first and second support legs are each forkshaped when viewed from the side by having a gap between two planar, parallel guide surfaces of each support leg, wherein in the gap the associated clamp arm is framed with planar outer guide surfaces in the manner of a hinge.

12. The fixing clamp according to claim 11, wherein the outer guide surfaces lie flat on each other and allow movement in one plane, wherein a hinge pin protrudes through an upper elongated hole of the end portion through the associated clamp arm as well as through a lower elongated hole that is congruent with the upper elongated hole.

13. An aligning device for a tibial resection guide comprising:
    a fixing clamp according to claim 1;
    an adjusting rod which is alignable with respect to a tibia of a patient; and
    a guiding device at a first end of the adjusting rod adapted to guide a tool during a resection of the tibia,
    the fixing clamp arranged at a second end of the adjusting rod, which grips and fixes the patient's tibia in order to fix the adjusting rod in relation to the tibia.

* * * * *